United States Patent [19]
Riley

[11] Patent Number: 6,048,504
[45] Date of Patent: Apr. 11, 2000

[54] PIN MAT FOR STERILIZATION TRAYS

[75] Inventor: Edward D. Riley, Falmouth, Me.

[73] Assignee: Riley Medical, Inc., Auburn, Me.

[21] Appl. No.: 09/145,075

[22] Filed: Sep. 1, 1998

[51] Int. Cl.$^7$ ........................................ A61L 2/00
[52] U.S. Cl. .................... 422/300; 206/438; 206/563; 422/297
[58] Field of Search .................... 206/438, 563; 15/215–217, 238–240, 161; 422/293, 297, 300

[56] References Cited

U.S. PATENT DOCUMENTS

| | | | |
|---|---|---|---|
| 3,605,166 | 9/1971 | Chen | 15/215 |
| 4,798,292 | 1/1989 | Hauze | 422/300 |
| 5,071,628 | 12/1991 | Alazet | 422/300 |
| 5,098,676 | 3/1992 | Brooks, Jr. | 422/292 |
| 5,211,915 | 5/1993 | Monch | 422/102 |
| 5,270,089 | 12/1993 | Alston et al. | 15/215 |
| 5,340,551 | 8/1994 | Berry, Jr. | 422/300 |
| 5,407,648 | 4/1995 | Allen et al. | 422/297 |
| 5,720,930 | 2/1998 | Bean | 422/300 |
| 5,766,561 | 6/1998 | Frieze et al. | 422/297 |
| 5,993,754 | 11/1999 | Lemmen et al. | 422/293 |

*Primary Examiner*—Krisanne Thornton
*Attorney, Agent, or Firm*—Cesari and McKenna, LLP

[57] ABSTRACT

A sterilization mat has a mesh-like backing with opposite faces composed of intersecting stringers defining relatively large openings in the backing. The stringers have rounded or inclined surfaces at one face of the backing and a multiplicity of resilient pins or fingers project from those surfaces for supporting and fixating medical instruments. Preferably, rounded or inclined surfaces are also provided at the underside of the backing. During sterilization, the mat minimizes the accumulation of condensed moisture on and under the mat and promotes efficient sterilization of the instruments on the mat.

10 Claims, 1 Drawing Sheet

PIN MAT FOR STERILIZATION TRAYS

This invention relates to sterilization mats. It relates more particularly to a pin mat for use in sterilization trays.

BACKGROUND OF THE INVENTION

A pin mat is a sheet-like article comprised of a backing and a multiplicity of resilient pins or fingers projecting from one face of the backing to provide a supporting bed for medical instruments, the instruments being held in place on the mat by the resilient pins or fingers. The mat is often associated with a sterilization tray having perforate walls to facilitate sterilizing instruments supported on the mat within the tray. During the sterilization process, a cover is placed over the open top of the tray and the tray is placed in an autoclave. High pressure steam injected into the autoclave enters the tray through the holes in the tray walls and comes into sterilizing contact with the instruments supported on the mat. Usually, the tray is provided with an antimicrobial filter which permits steam to enter and leave the tray but which excludes bacteria so that when the tray is removed from the autoclave, the tray contents remain in a sterilized condition.

When pin mats were originally placed in sterilization trays, it was found that the mat backing covered the vent holes in the bottom wall of the tray so that steam could only enter the tray through the holes in the tray side walls and cover. This tended to prolong the sterilization time. To avoid this problem, some mats were provided with holes in the mat backing and standoffs at the underside of the mat between the holes; see U.S. Pat. Nos. 5,098,676 and 5,766,561. With such constructions, the mat backing is spaced from the bottom wall of the sterilization tray so that steam is free to flow through the holes in the tray bottom wall and pass under the mat and through the holes in the mat into intimate contact with the instruments supported on the mat. The holes in the mat also allow for some drainage of condensed moisture from the mat.

While those prior mat constructions have reduced accumulated moisture on and under the mat and enabled somewhat shorter sterilization times, they still have certain disadvantages. More particularly, the prior mats have backings which are flat and the holes therein are relatively small so that fluids do not tend to flow along the surface of the mat. Therefore, during the sterilization process, condensed moisture can still form and collect on the upper surface of the backing between the holes therein. These small moisture pools provide sites for bacterial growth within the tray.

Another problem with conventional mats is due to the fact that their resilient pins or fingers are packed too densely. Resultantly, the instruments on the mat tend to rest on the tips of the pins rather than against the sides of the pins which would allow the pins to minimize lateral movements of the instruments on the mat. It follows also that if the pin count of the prior mats is excessive and the backing holes are smaller, the amount of material required to make those mats is also excessive.

SUMMARY OF THE INVENTION

Accordingly, it is an object of the present invention to provide an improved pin mat for use in sterilization trays.

Another object of the invention is to provide a pin mat which promotes the circulation of steam within a sterilization tray containing the mat.

Still another object of the invention is to provide a sterilization mat which discourages the accumulation of condensed moisture on the mat.

A further object of the invention is to provide a pin mat having an optimum distribution of pins for fixating a variety of different medical instruments.

Yet another object of the invention is to provide a sterilization mat which requires a minimum amount of material in order to make the mat.

Other objects will, in part, be obvious and will, in part, appear hereinafter.

The invention accordingly comprises the features of construction, combination of elements and arrangement of parts which will be exemplified in the following detailed description, and the scope of the invention will be indicated in the claims.

Briefly, my sterilization mat comprises a mesh-like backing having opposite faces and composed of intercepting stringers defining relatively large openings in the backing. The stringers have rounded or inclined surfaces at one face of the backing and a multiplicity of resilient pins or fingers project from those surfaces. Accordingly, any condensed moisture that drops onto the mat during the sterilization process will roll off the stringers onto the bottom wall of the sterilization tray and be drained away. Therefore, there can be no accumulation of condensed moisture on the mat.

Preferably, the stringers also have inclined or rounded surfaces at the opposite face of the mat so that when the mat is placed in a tray, there is minimum contact between the underside of the mat and the bottom wall of the tray so that steam can pass easily under the mat.

As will be described in more detail later, the mesh-like makeup of the mat backing means that the openings in the mat occupy a large percentage of the mat area. Accordingly, steam is able to circulate freely through the mat and the weight of the mat and thus the amount of material required to make the mat are kept to a minimum.

Finally, the spacing of the pins or fingers on my mat is appreciably larger than usual so that the mat is better able to fixate the instruments supported on the mat.

BRIEF DESCRIPTION OF THE DRAWINGS

For a fuller understanding of the nature and objects of the invention, reference should be had to the following detailed description taken in connection with the accompanying drawings, in which.

DETAILED DESCRIPTION OF THE PREFERRED EMBODIMENTS

Figure 1:
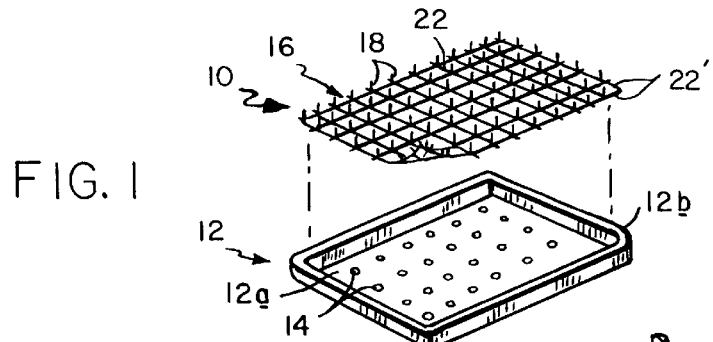
FIG. 1 is an exploded perspective view of a pin mat incorporating the invention shown in association with a sterilization tray.

Referring to FIG. 1 of the drawings, a pin mat indicated generally at 10 is shown in association with a sterilization tray indicated generally at 12, said tray having a bottom wall 12a and sidewalls 12b which walls are provided with a multiplicity of vent holes 14. Mat 10 is dimensioned and shaped to fit in tray 12, resting on the bottom wall 12a thereof. A cover (not shown) may be provided to close the open top of tray 12.

Figure 2:
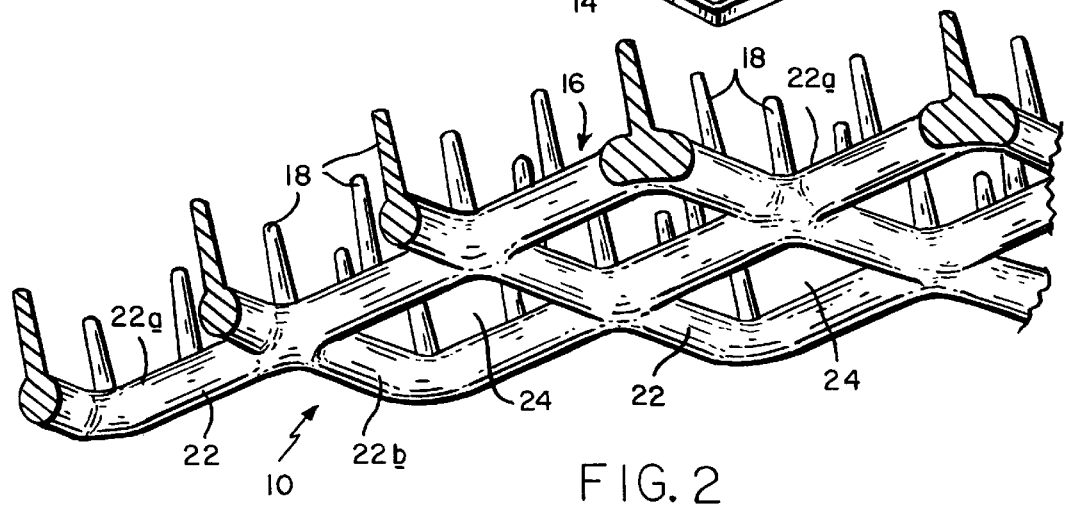
FIG. 2 is a fragmentary perspective view on a much larger scale showing the FIG. 1 mat in greater detail.

Referring to FIGS. 1 and 2, mat 10 comprises a grid or mesh-like backing 16 and a multiplicity of resilient pins or fingers 18 projecting from the upper face of the backing.

The mat backing 16 comprises a plurality of stringers or rods 22 which intersect to define an array of relatively large openings 24. In the illustrated mat, ribs 22 are arranged in columns and rows so that the openings 24 are generally rectangular in shape.

Figure 4A:
FIGS. 4A and 4B are crossectional views of alternative stringer shapes for the FIGS. 2 and 3 mats, respectively.

In accordance with the invention, the stringers 22 have rounded upper surfaces 22a, the pins 18 extending up from those surfaces. However, the stringers could just as well have triangular crossections; see FIG. 4A. The pins 18 are spaced apart along the stringers a sufficient distance such that medical instruments of different shapes and sizes placed on mat 10 can nestle against the sides of the pins and be fixated thereby.

Figure 4B:

The mat 10 specifically shown in FIG. 2 has stringers 22 which are more or less cylindrical. In other words, the stringers 22 have lower surfaces 22b which are essentially mirror images of the stringer upper surfaces 22a. Accordingly, when the mat 10 is positioned in tray 12, the stringers make only minimal line contacts with the tray bottom wall 12a. The same advantages would result if the stringers had diamond-shaped crossections; see FIG. 4B.

Mat 10 is preferably molded of a sterilizeable, medical grade, flexible, somewhat resilient material such as silicone. In a typical mat, the stringers may be about 1 inch long and 0.25 inch in diameter; the openings 24 may be 0.75 inch on a side and the fingers 18 may be 0.5 inches long and have a root diameter of 0.12 inch and a 3° taper and be spaced apart one inch or less. Preferably, the mat backing is designed so that the openings 24 occupy at least 40% of the mat area. Mat 10 may be cut from a larger sheet or roll of mat material to fit tray 12. Alternatively, the mat may be custom molded to fit tray 12 in which case it may be provided with stringers all around the mat perimeter as indicated at 22' in FIG. 1.

Figure 3:
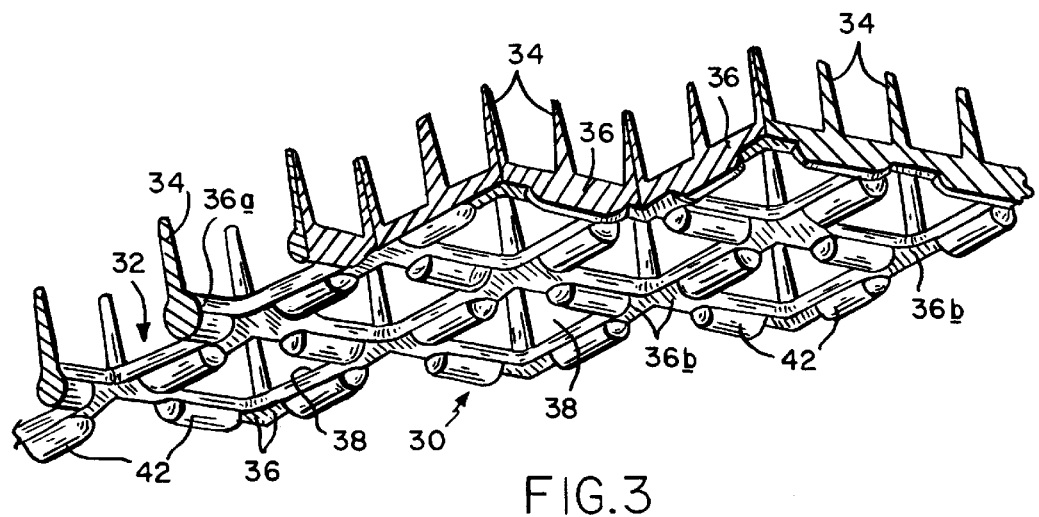
FIG. 3 is a view similar to FIG. 2 showing another embodiment of the mat.

Refer now to FIG. 3 which shows another mat embodiment indicated generally at 30. This embodiment also comprises a grid or mesh-like backing 32 which supports a bed of upstanding pins or fingers 34, those fingers being similar to fingers 18 in FIG. 2. Backing 32 is similar to backing 16 described above in that it is composed of intercepting stringers 36 which define an array of large openings 38, those stringers having curved upper surfaces 36a; they could just as well be inclined as in FIG. 4B. However, backing 32 differs from backing 16 in that the lower surfaces 36b of the stringers are flat and formed with a multiplicity of spaced-apart rounded beads or bosses 42 which function as stand-offs or spacers when the mat 30 is positioned in the tray 12 (FIG. 1). While the beads or bosses 42 are shown as being elongated, they could just as well be hemispheres inverted pyramids or any other shape that would provide minimum contact between mat 30 and the bottom wall 12a of tray 12.

In use, the mat 10 or 30 is positioned in tray 12 so that the mat rests on the tray bottom wall 12a. Due to the non-flat contact surfaces at the underside of the mat, the mat has limited contact with that wall. Furthermore, due to the open, mesh-like construction of the mat backing that provides large openings therein, there is no need to align those openings with the vent holes 14 in the tray as is required for the mat in the above U.S. Pat. No. 5,098,676. In other words, since the openings 24, 38 in the illustrated mats occupy almost half of the overall mat area, the mats present essentially no impediment to steam entering tray 12 through its holes 14. Thus, during the sterilization process, high pressure steam is free to circulate under and through the pin mat into intimate contact with medical instruments supported on the mat. Consequently, complete sterilization of those instruments can be accomplished in a minimum amount of time.

If condensed moisture should form within the tray, that moisture will drop down onto the rounded or inclined upper surfaces 22a, 36a of the mat backing and roll down the sides of the stringers 22, 36 into the bottom of tray 12 and be drained therefrom through the holes 14 therein. Thus, there can be no accumulation of moisture on or under the mat 10, 30 which could provide sites for bacterial growth on or under the mat.

Since the mats described herein are unitary, mesh-like molded plastic articles, they can be made in quantity relatively inexpensively using a minimum amount of material. Therefore, they should prove quite useful in hospitals, clinics and physicians' offices where instruments have to be sterilized prior to use.

It will thus be seen that the objects set forth above, among those made apparent from the preceding description, are efficiently attained. Also, certain changes may be made in the above constructions without departing from the scope of the invention. For example, the mat backing need not be a rectilinear mesh. The stringers or webs 22, 36 could just as well be shaped and oriented to form diamond-shaped or even circular openings. Also, the stringers themselves may have other crossectional shapes that would prevent the accumulation of condensed moisture on the top of the mat backing and provide minimum contact with the tray. For example, the stringers could have oral cross-sections. Therefore, it is intended that all matter contained in the above description or shown in the accompanying drawings shall be interpreted as illustrative and not in a limiting sense.

It is also to be understood that the following claims are intended to cover all of the generic and specific features of the invention described herein.

What is claimed is:

1. A sterilization mat comprising a an open-grid backing having opposite faces and composed of intersecting stringers defining openings in the backing, said stringers having rounded or inclined surfaces at one face of the backing and a multiplicity of resilient pins or fingers projecting from said inclined surfaces at said one face of the backing.

2. The mat defined in claim 1 wherein said mat is molded silicone.

3. The mat defined in claim 1 wherein said stringers also have rounded or inclined surfaces at the opposite face of the backing.

4. The mat defined in claim 3 wherein the stringers have substantially cylindrical or diamond-shaped cross sections.

5. The mat defined in claim 1 wherein the stringers have flat surfaces at the opposite face of the backing and further including a multiplicity of spaced-apart bosses projecting from the flat surfaces of the stringers.

6. The mat defined in claim 5 wherein the stringers have substantially semi-cylindrical or triangular cross sections.

7. The mat defined in claim 1 wherein the stringers are arranged in columns and rows so that said openings are substantially rectangular.

8. The mat defined in claim 1 wherein said fingers are tapered.

9. The mat defined in claim 1 wherein a plurality of said stringers define the perimeter of the backing.

10. The mat defined in claim 1 wherein said openings occupy at least 40% of the mat area.

* * * * *